United States Patent
Sadasivan Vijayakumari et al.

(10) Patent No.: US 8,895,792 B2
(45) Date of Patent: Nov. 25, 2014

(54) PROCESS FOR THE PREPARATION OF AN OLEFINIC PRODUCT COMPRISING ETHYLENE AND/OR PROPYLENE

(71) Applicant: Shell Oil Company, Houston, TX (US)

(72) Inventors: Sivakumar Sadasivan Vijayakumari, Amsterdam (NL); Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 14/136,047

(22) Filed: Dec. 20, 2013

(65) Prior Publication Data

US 2014/0187824 A1 Jul. 3, 2014

(30) Foreign Application Priority Data

Dec. 28, 2012 (EP) .................................... 12199599

(51) Int. Cl.
| | |
|---|---|
| *C07C 41/58* | (2006.01) |
| *C07C 29/76* | (2006.01) |
| *C07C 1/22* | (2006.01) |
| *C07C 11/04* | (2006.01) |
| *C07C 11/06* | (2006.01) |
| *C07C 1/20* | (2006.01) |
| *C07C 29/74* | (2006.01) |
| *C07C 31/04* | (2006.01) |

(52) U.S. Cl.
CPC ... *C07C 1/22* (2013.01); *C07C 1/20* (2013.01); *C07C 11/04* (2013.01); *C07C 29/74* (2013.01); *C07C 31/04* (2013.01); *C07C 11/06* (2013.01)
USPC ............ 585/324; 585/640; 568/699; 568/913

(58) Field of Classification Search
CPC ........................................................ C07C 1/22
USPC ............................ 568/699, 913; 585/324, 640
See application file for complete search history.

(56) References Cited

U.S. PATENT DOCUMENTS

| | | | | |
|---|---|---|---|---|
| 4,499,327 A | * | 2/1985 | Kaiser ............................ | 585/640 |
| 5,102,551 A | * | 4/1992 | Pasternak ...................... | 210/651 |
| 6,797,851 B2 | * | 9/2004 | Martens et al. ............... | 585/640 |
| 2011/0112344 A1 | * | 5/2011 | Chewter et al. ............... | 585/302 |

* cited by examiner

*Primary Examiner* — Sikarl Witherspoon

(57) ABSTRACT

An oxygenate to olefins (OTO) process, comprising the steps of: (i) purifying an oxygenate feedstream comprising one or more ionic contaminants by contacting the feedstream with a membrane, resulting in the formation of a retentate and a permeate separated by the membrane, which permeate is a purified oxygenate stream which contains a lower ionic contaminant concentration than the original oxygenate feedstream; (ii) introducing the purified oxygenate stream into an oxygenate to olefins reaction zone; and (iii) contacting the purified oxygenate stream with a molecular sieve catalyst in the oxygenate to olefins reaction zone to form a product stream comprising olefins.

16 Claims, No Drawings

US 8,895,792 B2

PROCESS FOR THE PREPARATION OF AN OLEFINIC PRODUCT COMPRISING ETHYLENE AND/OR PROPYLENE

This application claims the benefit of European Application No. 12199599.7 filed Dec. 28, 2012, which is incorporated herein by reference.

FIELD OF THE INVENTION

This invention relates to an oxygenate to olefins (OTO) process comprising a step of purifying an oxygenate feedstream, and to a process for purifying an oxygenate feedstream.

BACKGROUND TO THE INVENTION

There is a large market for light olefin products ethylene and propylene which are, for example, used in the production of plastics. Light olefins are traditionally produced via the cracking of petroleum feedstocks, e.g. through catalytic cracking, steam cracking, or some combination of the two processes. However, as petroleum feedstocks from crude oil face increasing prices, other sources of ethylene and propylene are becoming more attractive.

It is known to produce olefins from oxygenates via an oxygenate to olefins (OTO) process. Interest in OTO processes for producing ethylene and propylene is growing in view of the increasing availability of natural gas. Methane in the natural gas can, for example, be converted to methanol or dimethyl ether (DME), both of which are suitable oxygenate feedstocks for an OTO process. Oxygenates can also be produced from biomass.

In an OTO process, an oxygenate such as methanol is provided to a reaction zone comprising a suitable conversion catalyst, and converted to ethylene and propylene. In addition to the desired ethylene and propylene, a substantial part of the methanol is converted to higher hydrocarbons including C4+ olefins.

The catalyst is usually a molecular sieve catalyst. For example, U.S. Pat. No. 4,499,327 describes a process for making olefins from methanol using a silicoaluminophosphate (SAPO) molecular sieve catalyst. U.S. Pat. No. 6,797,851 describes a process for making ethylene and propylene from an oxygenate feed using two or more zeolite catalysts.

OTO processes can encounter problems due to the catalyst being fouled, for example due to coke deposition on the catalyst. Coke herein refers to a carbonaceous composition which next to the prevailing carbon may also contain hydrogen and other elements. Conventional catalyst regeneration techniques can be employed to remove the coke.

It has now been realised that the purity of the oxygenate feed may also affect the viability of the catalyst. In particular, the catalyst appears to be susceptible to deactivation by contaminants in the oxygenate feedstream such as metals.

US 2011/014404 describes a process for improving the quality of an oxygenate feedstream to an oxygenate to olefins conversion reactor by passing the feedstream to a feed fractionation column. This process therefore involves distilling the feedstream, in order to separate the oxygenate from undesired impurities such as sodium hydroxide (NaOH).

It is an aim of the invention to provide an improved oxygenate to olefins (OTO) process.

SUMMARY OF THE INVENTION

According to a first aspect of the present invention there is provided an oxygenate to olefins (OTO) process, comprising the steps of:

(i) purifying an oxygenate feedstream comprising one or more ionic contaminants by contacting the feedstream with a membrane, resulting in the formation of a retentate and a permeate separated by the membrane, which permeate is a purified oxygenate stream which contains a lower ionic contaminant concentration than the original oxygenate feedstream;

(ii) introducing the purified oxygenate stream into an oxygenate to olefins reaction zone; and (iii) contacting the purified oxygenate stream with a molecular sieve catalyst in the oxygenate to olefins reaction zone to form a product stream comprising olefins.

DETAILED DESCRIPTION

As known in the art, the retentate is a part of the oxygenate feedstream which does not pass through the membrane. The permeate is a part of the oxygenate feedstream which does pass through the membrane. The contacting of the oxygenate feedstream with a membrane in step (i) results in a permeate which has been purified in the sense that it will contain a lower ionic contaminant concentration, while the retentate will contain an increased ionic contaminant concentration, as compared to the original feedstream.

The inclusion of pretreatment step (i) in the OTO process can limit the catalyst being fouled, and can thus enhance the efficiency of the OTO process. Furthermore, using a membrane purification, as opposed to, for example, distillation, has the significant advantage that there is no need to change the phase of the oxygenate feedstream to be treated. This can save energy and requires less hardware.

In principle, the membrane can be any membrane consistent with the objective of forming a permeate which is a purified oxygenate stream which contains a lower ionic contaminant concentration than the original oxygenate feedstream.

In an embodiment, the membrane is a polymeric membrane.

In an embodiment, transmission of the permeate through the membrane in step (i) takes place via the solution-diffusion mechanism. As is known in the art, this means that the compounds to be permeated dissolve in a membrane matrix and diffuse through the membrane, after which they desorb into the permeate side. The main driving force for permeation may be hydrostatic pressure.

In an embodiment, the membrane is essentially non-porous. However, the process may alternatively also utilise nanoporous membranes, provided that a suitable rejection rate of ionic contaminants is achieved. In an embodiment, the membrane has a maximum pore size of at most 0.01 μm, such as at most 0.001 μm.

In an embodiment, the membrane is a polysiloxane membrane. In an embodiment, the membrane is a crosslinked polysiloxane membrane. Crosslinked polysiloxane membranes are reverse osmosis membranes that are essentially non-porous. The polysiloxane membranes are crosslinked to improve the membranes' resistance to dissolution of the membrane when it comes into contact with an oxygenate stream. In general, crosslinking of the relevant polysiloxanes can be effected in several ways, for instance by reaction with crosslinking agents, and can optionally be enhanced by irradiation.

The polysiloxanes which may be crosslinked can contain repeating units of the formula (I):

$$-[Si(R)(R')O]n- \qquad (I)$$

In the above formula, R and R' may be the same or different and represent hydrogen or a hydrocarbon group, which hydrocarbon group may be selected from the group consisting of alkyl (optionally substituted with one or more aryl groups), cycloalkyl (optionally substituted with one or more alkyl or aryl groups) and aryl (optionally substituted with one or more alkyl groups).

In an embodiment, at least one of the groups R and R' is an alkyl group. In an embodiment, at least one of the groups R and R' is a C1-12 alkyl group, such as a C1-8 alkyl group. In an embodiment, both R and R' are octyl groups. In an embodiment, both R and R' are methyl groups.

In an embodiment, the polysiloxanes are —OH and/or —NH2 terminated polysiloxanes. In an embodiment, the polysiloxanes are —OH and/or —NH2 terminated polydimethylsiloxanes.

Crosslinking can be effected through the reactive terminal —OH and/or —NH2 groups of the polysiloxanes.

Examples of suitable crosslinked polysiloxane membranes are described in U.S. Pat. No. 5,102,551.

In an embodiment, the crosslinked polysiloxane membrane is a crosslinked polydimethylsiloxane (PDMS) membrane.

In an embodiment, the membrane has a thickness of from 0.5 to 15 μm, from 1 to 15 μm, from 0.5 to 10 μm, from 1 to 10 μm, from 0.5 to 5 μm, or from 1 to 5 μm.

The membrane can be supported on at least one substrate layer. This can provide mechanical strength. The resulting membranes can be referred to as composite membranes or thin film composites. Generally, such a composite membrane may be composed of a membrane supported on a porous substrate layer. The porous substrate layer may have been treated with a pore protector prior to coating it with, for example, a polysiloxane layer which is subsequently crosslinked to form the membrane. The porous substrate layer may in return be supported on a further porous support, for example to provide additional mechanical strength. The membrane may also be used without a substrate layer and/or support, but it will be understood that in such a case the thickness of the membrane should be sufficient to withstand the pressures applied; a thickness greater than 10 μm may then be required. Such a thick membrane can significantly limit the throughput of the membrane, thereby decreasing the amount of purified product which can be recovered per unit of time and membrane area.

The porous substrate layer can provide mechanical strength to the membrane. Examples of suitable materials for the porous substrate layer include polyacrylonitrile (PAN), polyamide imide, polyamide imide+TiO2 (PAT), polyether imide (PEI), polyvinylidene fluoride, polyvinylidene difluoride (PVDF), and porous polytetrafluoroethylene (PTFE).

As mentioned above, the porous substrate layer may have been treated with a pore protector prior to coating it with, for example, a polysiloxane layer which is subsequently crosslinked to form the membrane. This pore protector may, for example, be a hydroxyterminated polysiloxane.

In an embodiment, the oxygenate feedstream used in the process according to the invention comprises an oxygenate containing at least one oxygen-bonded alkyl group, such as a C1-C5 alkyl group, for example a C1-C4 alkyl group. In an embodiment, the alkyl group comprises 1 or 2 carbon atoms, for example one carbon atom.

Examples of oxygenates that can be used in the oxygenate feedstream include alcohols and ethers. In an embodiment, the oxygenate feedstream comprises one or more oxygenates selected from the group consisting of alcohols, such as methanol, ethanol, and propanol; and dialkyl ethers, such as dimethylether, diethylether and methylethyether.

In an embodiment, the oxygenate feedstream comprises methanol or dimethylether, or a mixture thereof. In an embodiment, the oxygenate feedstream comprises methanol.

In an embodiment, the oxygenate feedstream comprises at least 50 wt % of oxygenate, for example methanol and/or dimethylether, based on total hydrocarbons. In an embodiment, the oxygenate feedstream comprises at least 70 wt % of oxygenate, for example methanol and/or dimethylether, based on total hydrocarbons. In an embodiment, the oxygenate feedstream consists or consists essentially of oxygenate, for example methanol and/or dimethylether.

In an embodiment, the oxygenate is obtained as a reaction product of synthesis gas. Synthesis gas can for example be generated from fossil fuels, such as from natural gas or oil, or from the gasification of coal. Suitable processes for this purpose are for example discussed in Industrial Organic Chemistry, Klaus Weissermehl and Hans-Jürgen Arpe, 3rd edition, Wiley, 1997, pages 13-28. This book also describes the manufacture of methanol from synthesis gas on pages 28-30.

In an embodiment, the oxygenate is obtained from biomaterials, such as through fermentation, for example by a process as described in DE 10043644.

In an embodiment, at least part of the oxygenate feedstream is obtained by converting methane into synthesis gas. The methane can be obtained from natural gas or associated gas.

The oxygenate feedstream in step (i) may be provided directly from one or more oxygenate synthesis zones, or it may be provided from an oxygenate storage facility.

The oxygenate feedstream comprises one or more ionic contaminants. In an embodiment, the one or more ionic contaminants in the oxygenate feedstream comprise metal ions. In an embodiment, the metal ions comprise sodium ions.

The permeate which is formed in step (i) is a purified oxygenate stream which contains a lower ionic contaminant concentration than the original oxygenate feedstream. The electrical conductance, as measured by units of Siemens, is therefore lower for the permeate than for the oxygenate feedstream.

In an embodiment, one or more ionic contaminants in the oxygenate feedstream are present in an amount of up to 0.5 wt % based on the total weight of the oxygenate feedstream, or up to 0.3 wt %, or up to 0.1 wt %, or up to 0.01 wt %. In an embodiment, one or more ionic contaminants in the oxygenate feedstream are present in an amount of at least 0.00001 wt % based on the total weight of the oxygenate feedstream, or at least 0.0001 wt %. In an embodiment, one or more ionic contaminants in the oxygenate feedstream are present in an amount of from 0.00001 wt % to 0.5 wt %, from 0.00001 wt % to 0.3 wt %, from 0.00001 wt % to 0.1 wt %, from 0.00001 wt % to 0.01 wt %, from 0.0001 wt % to 0.5 wt %, from 0.0001 wt % to 0.3 wt %, from 0.0001 wt % to 0.1 wt %, or from 0.0001 wt % to 0.01 wt %.

In an embodiment, in step (i) of the process according to the first aspect of the present invention, at least 80% of one or more ionic contaminants are removed from the oxygenate feedstream. In an embodiment, this is at least 85%, at least 90%, at least 95%, or at least 99%.

In an embodiment, any ionic contaminants remaining in the purified oxygenate stream after step (i) are present in an amount of less than 0.1 wt %, or less than 0.01 wt %, or less than 0.001 wt %, or less than 0.0001 wt %, or less than 0.00001 wt %, or less than 0.00001 wt %, or less than 0.000001 wt %.

In an embodiment, during contacting of the oxygenate feedstream with the membrane in accordance with step (i) of the process according to the first aspect of the invention, the pressure difference across the membrane can, for example, be from 2 to 80 bar, from 5 to 80 bar, from 10 to 80 bar, from 20 to 80 bar, from 30 to 80 bar, from 2 to 60 bar, from 5 to 60 bar, from 10 to 60 bar, from 20 to 60 bar, from 30 to 60 bar, from 2 to 50 bar, from 5 to 50 bar, from 10 to 50 bar, from 20 to 50 bar, or from 30 to 50 bar.

In an embodiment, if the oxygenate feedstream comprises methanol and it is desired for methanol to permeate, the pressure difference across the membrane can, for example, be from 10 to 60 bar, from 20 to 60 bar, from 30 to 60 bar, from 10 to 50 bar, from 20 to 50 bar, or from 30 to 50 bar, such as around 40 bar.

In an embodiment, if the oxygenate feedstream comprises methanol and water and it is desired for both methanol and water to permeate, the pressure difference across the membrane can, for example, be at least 40 bar, such as at least 45 bar, for example at least 50 bar.

Throughout this specification, unless indicated otherwise, references to pressures are to absolute pressures.

In an embodiment, in step (i) the oxygenate feedstream is contacted with the membrane at a temperature below 100° C., such as a temperature in the range of from 10 to 80° C., for example from 10 to 40° C. In an embodiment, the temperature is about room temperature.

In principle every known oxygenate to olefins (OTO) conversion system and process can be used in conjunction with the pretreatment step (i), including more specific processes known as Methanol to Olefins (MtO) and Methanol to Propylene (MtP).

In an embodiment, the molecular sieve catalyst in step (iii) comprises one or more catalysts selected from the group consisting of zeolite catalysts, silicoaluminophosphate (SAPO) catalysts, aluminophosphate (AlPO) catalysts and metal substituted (silico)aluminophosphate (MeAlPO) catalysts. In an embodiment, the molecular sieve catalyst comprises one or more zeolite catalysts.

Molecular sieve catalysts typically also include binder materials, matrix material and optionally fillers. Matrix materials can, for example, include clays such as kaolin. Binder materials can, for example, include silica, alumina, silica-alumina, titania and zirconia. Silica has the advantage of low acidity.

The molecular sieve catalysts can have a molecular framework of one, two or more corner-sharing tetrahedral units, for example two or more $[SiO_4]$, $[AlO_4]$ and/or $[PO_4]$ tetrahedral units. These silicon, aluminium and/or phosphorous based molecular sieves and metal containing silicon, aluminium and/or phosphorous based molecular sieves have been described in, for example, U.S. Pat. No. 4,567,029. In an embodiment, the molecular sieve catalysts have 8-, 10- or 12-ring structures and an average pore size in the range of from 3 Å to 15 Å.

In an embodiment, the molecular sieve catalyst comprises an aluminosilicate-comprising catalyst, such as a zeolite-comprising catalyst. In a zeolite-comprising catalyst the amount of zeolite can suitably be from 20 to 50 wt %, such as from 35 to 45 wt %, based on the total catalyst composition.

Examples of suitable zeolite catalysts include those containing a zeolite of the ZSM group, such as those of the MFI type, such as ZSM-5; the MTT type, such as ZSM-23; the TON type, such as ZSM-22; the MEL type, such as ZSM-11; and the FER type. Other examples of suitable zeolites are zeolites of the STF-type, such as SSZ-35; the SFF type, such as SSZ-44; and the EU-2 type, such as ZSM-48.

In an embodiment, the molecular sieve catalyst comprises a more-dimensional zeolite, such as those of the MFI type, for example ZSM-5; or of the MEL type, such as zeolite ZSM-11. A zeolite having more-dimensional channels has intersecting channels in at least two directions. So, for example, the channel structure is formed of substantially parallel channels in a first direction, and substantially parallel channels in a second direction, wherein channels in the first and second directions intersect. Intersections with a further channel type are also possible. In an embodiment, the channels in at least one of the directions are 10-membered ring channels. In an embodiment, the molecular sieve catalyst comprises a MFI-type zeolite having a silica-to-alumina ratio (SAR) of at least 60, for example at least 80.

Examples of the molecular sieve catalyst include catalysts comprising one or more zeolites having one-dimensional 10-membered ring channels, e.g. one-dimensional 10-membered ring channels which are not intersected by other channels.

In an embodiment, the molecular sieve catalyst comprises zeolites of the MTT and/or TON type.

In an embodiment, the molecular sieve catalyst comprises in addition to one or more one-dimensional zeolites having 10-membered ring channels, such as zeolites of the MTT and/or TON type; a more-dimensional zeolite, such as zeolites of the MFI type, for example ZSM-5.

The catalyst may comprise phosphorus as such, i.e. in elemental form, or in a compound, i.e. phosphorous other than any phosphorus included in the framework of the molecular sieve. In an embodiment, an MEL or MFI-type zeolites comprising catalyst additionally comprises phosphorus. The phosphorus may be introduced by pre-treating the MEL or MFI-type zeolites prior to formulating the catalyst and/or by post-treating the formulated catalyst comprising the MEL or MFI-type zeolites. In an embodiment, the catalyst comprising MEL or MFI-type zeolites comprises phosphorus as such or in a compound in an elemental amount of from 0.05 to 10 wt % based on the weight of the formulated catalyst. In an embodiment, the catalyst comprises phosphor and MEL or MFI-type zeolites having a silica-to-alumina ratio (SAR) in the range of from 60 to 150, such as from 80 to 100. In an embodiment, the catalyst comprises phosphorus and ZSM-5 having a SAR in the range of from 60 to 150, such as from 80 to 100. In an embodiment, the catalyst comprises phosphorus-treated MEL or MFI-type zeolites having a SAR in the range of from 60 to 150, such as from 80 to 100. In an embodiment, the catalyst comprises phosphorus-treated ZSM-5 having a SAR in the range of from 60 to 150, such as from 80 to 100.

In an embodiment, the molecular sieve catalyst comprises molecular sieves which are used in the hydrogen form, for example HZSM-22, HZSM-23, HZSM-48 and/or HZSM-5. In an embodiment, at least 50% w/w, such as at least 90% w/w, for example at least 95% w/w or 100% of the total amount of molecular sieves used is in the hydrogen form. It is well known in the art how to produce such molecular sieves in the hydrogen form.

Examples of silicoaluminophosphate catalysts include SAPO-17, SAPO-18, SAPO-34, SAPO-35, and SAPO-44, and SAPO-5, SAPO-8, SAPO-11, SAPO-20, SAPO-31, SAPO-36, SAPO-37, SAPO-40, SAPO-41, SAPO-42, SAPO-47 and SAPO-56.

For metal substituted (silico)aluminophosphate (MeAlPO) catalysts, the Me in MeAlPO refers to a substituted metal atom, such as a metal selected from one of Group IA, IIA, IB, IIIB, IVB, VB, VIB, VIIB, VIIIB and the Lanthanides of the Periodic Table of Elements. In an embodiment, the metal is selected from one of the group consisting of Co, Cr, Cu, Fe, Ga, Ge, Mg, Mn, Ni, Sn, Ti, Zn and Zr.

The catalyst particles used in the process of the present invention can have any shape known to the skilled person to be suitable for this purpose. The catalyst can, for example, be present in the form of spray dried catalyst particles, spheres, tablets, rings, extrudates, etc. Extruded catalysts can be applied in various shapes, such as, for example, cylinders and trilobes. Spherical particles are normally obtained by spray drying. In an embodiment, the weight average particle size is in the range of 1-500 μm, such as 50-100 μm.

In step (iii) of the process according to the first aspect of the invention, the purified oxygenate stream is reacted or converted to form a product stream comprising ethylene and/or propylene in an oxygenate-to-olefins (OTO) process. In an embodiment, the product stream additionally comprises catalyst that is at least partially coked; the catalyst can be separated from the rest of the product stream as discussed below.

The reaction conditions in the oxygenate to olefins reaction zone in step (iii) may include a reaction temperature of from 350 to 1000° C., such as from 350 to 750° C., for example from 450 to 750° C. In an embodiment, the reaction temperature is from 450 to 700° C., such as from 500 to 650° C.

The reaction conditions in the oxygenate to olefins reaction zone in step (iii) may further include a pressure from 1 bar to 50 bar, such as from 1 to 15 bar, for example from 1 to 4 bar. In an embodiment, the pressure is from 1.1 to 3 bar, such as from 1.3 to 2 bar.

In an embodiment, the purified oxygenate stream is preheated to a temperature in the range of from 120 to 550° C., such as from 250 to 500° C., prior to introducing it into the oxygenate to olefins reaction zone in step (ii).

The purified oxygenate stream can be introduced into the oxygenate to olefins reaction zone together with a diluent, such as nitrogen and water, for example in the form of steam. In an embodiment, the molar ratio of oxygenate to diluent is between 10:1 and 1:10. In an embodiment, this ratio is between 4:1 and 1:2. In an embodiment, the molar ratio of oxygenate to diluent is between 4:1 and 1:2, the purified oxygenate stream comprises methanol and the diluent is water (steam).

In an embodiment, in step (ii) of the process according to the first aspect of the invention, an olefinic co-feed is introduced into the oxygenate to olefins reaction zone along with the purified oxygenate stream. The olefinic co-feed can be provided separately from the purified oxygenate stream or as part of the purified oxygenate stream. In the case where the oxygenate stream comprises methanol, such a process can be referred to as an Olefin-assisted Methanol to Olefins (OMO) process.

The purified oxygenate stream and/or the olefinic co-feed may be introduced into the oxygenate to olefins reaction zone together with a diluent, such as nitrogen and water, for example in the form of steam, as discussed above.

Reference herein to an olefinic co-feed is to an olefin-comprising co-feed.

One or more olefins (olefin species) may be introduced into the OTO reaction zone by the olefinic co-feed.

In an embodiment, the olefinic co-feed comprises C4 and higher olefins (C4+ olefins), such as C4 to C8 olefins, e.g. C4 and C5 olefins. In an embodiment, the olefinic co-feed comprises at least 25 wt %, such as at least 50 wt %, of C4+ olefins, such as C4 olefins, e.g. butene. The olefinic co-feed may optionally also comprise propylene. In an embodiment, the olefin component is substantially free from ethylene and propylene.

In an embodiment, the olefinic co-feed comprises at least 10 wt % of one or more olefins, such as C4+ olefins, based on total hydrocarbons. In an embodiment, the olefinic co-feed comprises at least 50 wt % of one or more olefins, such as C4+ olefins, based on total hydrocarbons. In an embodiment, the olefinic co-feed comprises at least a total of 70 wt % of C4 hydrocarbon species. In an embodiment, the olefinic co-feed consists or consists essentially of one or more olefins specified herein.

The first aspect of the invention therefore provides a process in which a feed comprising an oxygenate component, and optionally an olefin component, is converted to a product stream comprising ethylene and/or propylene.

The feed is reacted in the oxygenate to olefins (OTO) reaction zone in the presence of a molecular sieve catalyst to form a product stream comprising ethylene and/or propylene; the reaction ensures that the product stream is enriched in ethylene and/or propylene compared to the feed. Typically both ethylene and propylene are present in the product stream, which typically also comprises catalyst that is at least partially coked.

The olefinic co-feed may advantageously be a recycle stream (discussed in more detail below).

In an embodiment, in step (ii) an olefinic co-feed is introduced into the oxygenate to olefins reaction zone along with the purified oxygenate stream and the molecular sieve catalyst is an aluminosilicates-comprising catalyst, such as a zeolite-comprising catalyst. These types of catalysts are particularly suitable when an olefinic co-feed is fed to the oxygenate to olefins reaction zone together with oxygenate, and their use can lead to increased production of ethylene and propylene. In an embodiment, the molecular sieve catalyst comprises a more-dimensional zeolite, such as those of the MFI type, for example ZSM-5; or of the MEL type, such as zeolite ZSM-11. Such zeolites are particularly useful for converting olefins, including iso-olefins, to ethylene and/or propylene.

The reaction in step (iii) may suitably be operated in a fluidized bed, e.g. a dense, turbulent or fast fluidized bed or a riser reactor system, or in a fixed bed reactor, moving bed reactor or a tubular reactor. In an embodiment, the reaction is operated in a fluidized bed, e.g. a turbulent fluidized bed, fast fluidized bed or a riser reactor or downward reactor system.

The superficial velocity of the gas components in a dense fluidized bed will generally be from 0 to 1 m/s; the superficial velocity of the gas components in a turbulent fluidized bed will generally be from 1 to 3 m/s; the superficial velocity of the gas components in a fast fluidized bed will generally be from 3 to 5 m/s; and the superficial velocity of the gas components in a riser reactor will generally be from 5 to about 25 m/s.

It will be understood that dense, turbulent and fast fluidized beds will include a dense lower reaction zone with densities generally above 300 kg/m$^3$. Moreover, when working with a fluidized bed several possible configurations can be used: (a) co-current flow meaning that the gas (going upward) and the catalyst travels through the bed in the same direction, and (b) countercurrent, meaning that the catalyst is fed at the top of the bed and travels through the bed in opposite direction with respect to the gas, whereby the catalyst leaves the vessel at the bottom. In a conventional riser reactor system the catalyst and the vapours will travel co-currently.

In an embodiment, a fluidized bed, such as a turbulent fluidized bed system, e.g. a riser reactor, is used. Suitably, in such a riser reactor the purified oxygenate stream is contacted with the molecular sieve catalyst at a weight hourly space velocity of at least 1 hr$^{-1}$, such as from 1 to 1000 hr$^{-1}$, for example from 1 to 500 hr$^{-1}$, from 1 to 250 hr$^{-1}$, from 1 to 100 hr$^{-1}$, or from 1 to 50 hr$^{-1}$.

In step (iii) of the process, use can be made of a single reactor with a stacked bed configuration wherein a first stage is carried out in a first zeolite catalyst bed and a second stage is carried out a second zeolite bed (see e.g. FIG. 1 of U.S. Pat. No. 6,797,851). Alternatively, the two stages can be carried out in two separate reactors (see e.g. FIGS. 2-5 of U.S. Pat. No. 6,797,851).

As mentioned above, the product stream from step (iii) may additionally comprise catalyst that is at least partially coked. In that case, the process may further comprise a step (iv) in which the catalyst is separated from the rest of the product stream to obtain olefins.

The separation in step (iv) can, for example, be carried out by one or more cyclone separators. Such cyclone separators are well known in the art. Other methods for separating the catalyst from the olefins can also be used, e.g. methods that apply plates, caps, elbows, and the like.

Olefins may be recovered from the product stream obtained in step (iv) in a recovery step (v). The olefins as recovered in step (v) may be separated into at least one olefinic product fraction containing ethylene and/or propylene and one or more further olefinic fractions containing olefins having four or more carbon atoms, which further olefinic fraction(s) may be at least partly recycled to step (iii) for use as a recycle stream providing the olefinic co-feed.

In an embodiment, at least 70 wt % of the olefinic co-feed, based on the whole olefinic co-feed, is formed by the recycle stream of the one or more further olefinic fractions containing olefins having four or more carbon atoms. In an embodiment, at least 90 wt % of the olefinic co-feed is formed by such recycled olefins.

In order to maximize production of ethylene and propylene, it is desirable to optimize the recycle of C4 olefins. This can be done by recycling only a part of the one or more further olefinic fractions containing olefins having four or more carbon atoms, such as the C4-C5 hydrocarbon fraction, e.g. the C4 hydrocarbon fraction, to the OTO reaction zone. Suitably, however, a certain part of the further fractions, such as between 1 and 5 wt %, is withdrawn as purge, since otherwise saturated hydrocarbons, in particular C4 hydrocarbons (butane) would build up in the process, which are substantially not converted under the OTO or reaction conditions.

In an embodiment, the olefins as recovered in step (v) are subjected to a quenching treatment before they are separated into at least one olefinic product fraction containing ethylene and/or propylene and one or more further olefinic fractions. In such a quenching treatment, water and C6+ hydrocarbons can be removed from the olefins. Suitably, the olefins are subjected to a heat recovery step before they are subjected to the quenching treatment. In an embodiment, olefins obtained after the quenching treatment are first compressed before they are separated into at least one olefinic product fraction containing ethylene and/or propylene and one or more further olefinic fractions. Instead of a quenching treatment of the olefins, use can alternatively be made of air coolers to bring down the temperature of the olefins.

In an embodiment, preceding to step (i) of the process according to the first aspect of the invention, the oxygenate in the oxygenate feedstream has been transported by sea. This mode of transportation is prone to allowing the oxygenate to pick up ionic contaminants such as metal ions, for example sodium ions. Oxygenate which has been transported by sea would, therefore, benefit particularly from pretreatment step (i) before being used in an oxygenate to olefins process.

It is to be understood that the process of the invention may be readily adapted and may include intermediate steps not explicitly specified herein. For example, in an embodiment, the purified oxygenate stream from step (i) may undergo one or more intermediate steps before being introduced into the oxygenate to olefins reaction zone in step (ii). For example, particularly if the original oxygenate feedstream comprises methanol, and step (i) results in a purified methanol stream, before being introduced into the oxygenate to olefins reaction zone, the purified methanol stream may be used to wash out dimethyl ether from the product stream from the oxygenate to olefins reaction zone. The resulting stream comprising both methanol and dimethyl ether can then be introduced into the oxygenate to olefins reaction zone in step (ii).

Of course step (i) of the process can also be used independently, if desired, e.g. wherever a purified oxygenate stream is required. From a second aspect of the present invention there is provided a process for purifying an oxygenate feedstream, comprising the step of contacting the feedstream with a membrane, preferably a polymeric membrane, resulting in the formation of a retentate and a permeate separated by the membrane, which permeate is a purified oxygenate stream which contains a lower ionic contaminant concentration than the original oxygenate feedstream.

Embodiments and optional features described hereinabove in relation to step (i) of the process according to the first aspect of the invention may also be applied to the process according to the second aspect of the invention.

Throughout the description and claims of this specification, the words "comprise" and "contain" and variations of the words, for example "comprising" and "comprises", mean "including but not limited to", and do not exclude other moieties, additives, components, integers or steps. Moreover the singular encompasses the plural unless the context otherwise requires: in particular, where the indefinite article is used, the specification is to be understood as contemplating plurality as well as singularity, unless the context requires otherwise.

Preferred features of each aspect of the invention may be as described in connection with any of the other aspects. Generally speaking the invention extends to any novel one, or any novel combination, of the features disclosed in this specification (including any accompanying claims and drawings). Thus features, integers, characteristics, compounds, chemical moieties or groups described in conjunction with a particular aspect, embodiment or example of the invention are to be understood to be applicable to any other aspect, embodiment or example described herein unless incompatible therewith. Moreover unless stated otherwise, any feature disclosed herein may be replaced by an alternative feature serving the same or a similar purpose.

Where upper and lower limits are quoted for a property, then a range of values defined by a combination of any of the upper limits with any of the lower limits may also be implied.

In this specification, references to component properties are—unless stated otherwise—to properties measured under ambient conditions, ie at atmospheric pressure and at a temperature of from 16 to 22 or 25° C., or from 18 to 22 or 25° C., for example about 20° C.

We claim:
1. An oxygenate to olefins (OTO) process, comprising the steps of:
 (i) purifying an oxygenate feedstream comprising one or more ionic contaminants by contacting the feedstream with a membrane, resulting in the formation of a retentate and a permeate separated by the membrane, which permeate is a purified oxygenate stream which contains a lower ionic contaminant concentration than the original oxygenate feedstream;

(ii) introducing the purified oxygenate stream into an oxygenate to olefins reaction zone; and (iii) contacting the purified oxygenate stream with a molecular sieve catalyst in the oxygenate to olefins reaction zone to form a product stream comprising olefins.

2. The process of claim 1, wherein the membrane is a polymeric membrane.

3. The process of claim 1, wherein transmission of the permeate through the membrane in step (i) takes place via a solution-diffusion mechanism.

4. The process of claim 3, wherein the membrane is a crosslinked polysiloxane membrane.

5. The process of claim 4, wherein the crosslinked polysiloxane membrane, comprises a crosslinked polydimethylsiloxane (PDMS) membrane.

6. The process of claim 1, wherein the oxygenate feedstream comprises methanol and/or dimethyl ether.

7. The process of claim 1, wherein the one or more ionic contaminants in the oxygenate feedstream comprise metal ions.

8. The process of claim 7, wherein the metal ions comprise sodium ions.

9. The process of claim 1, wherein the molecular sieve catalyst comprises one or more catalysts selected from the group consisting of zeolite catalysts, silicoaluminophosphate (SAPO) catalysts, aluminophosphates (AlPO) catalysts and metal substituted (silico)aluminophosphate (MeAlPO) catalysts.

10. The process of claim 9, wherein the molecular sieve catalyst comprises one or more zeolite catalysts.

11. The process of claim 1, wherein the molecular sieve catalyst is used in the hydrogen form.

12. The process of claim 11, wherein the molecular sieve catalyst comprises HZSM-22, HZSM-23, HZSM-48 and/or HZSM-5.

13. The process of claim 1, wherein in step (ii), an olefinic co-feed is introduced into the oxygenate to olefins reaction zone along with the purified oxygenate stream.

14. The process of claim 1, wherein preceding step (i), the oxygenate in the oxygenate feedstream has been transported by sea.

15. A process for purifying an oxygenate feedstream comprising one or more ionic contaminants, comprising the step of contacting the feedstream with a polymeric membrane resulting in the formation of a retentate and a permeate separated by the membrane, which permeate is a purified oxygenate stream which contains a lower ionic contaminant concentration than the original oxygenate feedstream.

16. The process of claim 15, wherein the polymeric membrane is a crosslinked polysiloxane membrane.

* * * * *